United States Patent [19]

Burgin

[11] 4,165,746

[45] Aug. 28, 1979

[54] PLASTIC FORCEPS

[76] Inventor: Kermit H. Burgin, R.R. #1, Box 334, Whitestown, Ind. 46075

[21] Appl. No.: 811,550

[22] Filed: Jun. 30, 1977

[51] Int. Cl.² .................. A61B 17/28; A61B 1/06; A61B 1/32
[52] U.S. Cl. ................................ 128/321; 81/302; 81/423; 128/18
[58] Field of Search ............... 128/321, 17, 18, 20, 128/345, 322, 323; 81/302, 43, 421, 422, 423

[56] References Cited

U.S. PATENT DOCUMENTS

| 399,749 | 3/1889 | Galiano | 128/323 |
| 776,302 | 11/1904 | Crockett | 128/17 |
| 1,094,575 | 4/1914 | Joutras | 128/18 |
| 2,544,932 | 3/1951 | Marco | 128/17 |
| 3,503,398 | 3/1970 | Fogarty et al. | 128/322 X |
| 3,853,120 | 12/1974 | Batista | 128/20 |

FOREIGN PATENT DOCUMENTS

| 641915 | 8/1928 | France | 128/321 |
| 246611 | 4/1926 | Italy | 128/321 |

OTHER PUBLICATIONS

Surg., Gynec. and Obstetrics, vol. 68, No. 6, Jan. 1939, pp. 1060–1063.

Primary Examiner—Robert W. Michell
Assistant Examiner—Michael H. Thaler
Attorney, Agent, or Firm—Jenkins, Coffey, Hyland, Badger & Conard

[57] ABSTRACT

A pair of disposable plastic forceps includes elongated arms, each having a proximal end portion providing a handle and a distal end portion for attachment of a contacting member to each of the arms, and a hinge for movably connecting the arms to one another to provide adjustment of the forceps, the hinge joining the arms intermediate their ends. Desirably, the hinge rotatably and frictionally receives the intermediate portion of each arm to hold the arms in position relative to the hinge after they are adjusted. The distal end of each arm is formed to provide a slot for removably receiving a contacting member. Contacting members of various sizes and shapes are provided, the size and shape selected being dependent in part upon the function to be performed by the forceps. The slot in each arm is defined by a pair of opposed walls. The contacting members include side walls which engage the opposed walls of the slot. Either the walls of the slot or the side walls of the contacting member can be provided with opposed raised bearing surfaces, the remaining pair of walls being provided with indentations to provide a snap-fit of the contacting members into the slots and pivotal frictional contact of the contacting members relative to the ends of the arms. In this manner, the contacting members can be adjusted on the ends of the arms, or can readily be exchanged for contacting members having a different size and/or shape.

10 Claims, 18 Drawing Figures

PLASTIC FORCEPS

This invention relates to an apparatus for dilating a meatus or incision, and particularly to disposable plastic forceps having quickly and readily interchangeable contacting members and frictional adjustment means incorporated therein.

There are many well-known specula and forceps for opening or enlarging body orifices or incisions. See for example, the following U.S. patents: Molesworth, U.S. Pat. No. 400,589; Crockett, U.S. Pat. No. 776,302; Joutras, U.S. Pat. No. 1,094,575; Pomerene, U.S. Pat. No. 1,170,324; and, Radcliff, U.S. Pat. No. 2,217,968. The devices of all of these patents require sterilization between uses. Further, such devices are not adaptable to use in orifices or incisions having different sizes, shapes, depths and so forth.

It is an object of the present invention to provide forceps which are economical to manufacture, such that they can be disposed of after one or several uses, and are divisible into contacting portions which contact the interior of the body upon which the forceps are used, and generally non-contacting portions which do not, and therefore, need not be disposed of. Further, these non-contacting portions can be sterilized by any suitable method.

According to the present invention, there is provided a simple and inexpensive means to attach the contacting portions of the forceps to the non-contacting portion, such that contacting portions are easily and readily interchangeable to accommodate different sizes, shapes and depths of meatuses and incisions. The various sizes and shapes of contacting members are so constructed that they can be inexpensively manufactured. The contacting members are readily attached to, and removed from, the non-contacting members of the forceps.

According to the illustrated embodiment of the invention, disposable plastic forceps include a pair of elongated arms, each having a proximal end portion providing a handle and a distal end portion for attachment of a contacting member to each of the arms. A hinge movably joins the arms to one another to provide adjustment of the forceps, the hinge joining the arms intermediate their ends. The hinge rotatably and frictionally receives the intermediate portion of each arm to hold the arms in selected positions relative to the hinge.

According to two illustrated embodiments, the distal end of each arm is formed to provide means for removably connecting the contacting members. In these embodiments, the removable connecting means comprises a slot formed in the distal end of each arm. The slot has two facing side walls which extend generally longitudinally of the distal end of the arm, the facing side walls cooperating with two opposed side walls of the contacting member to provide a snap-fit of the contacting members into the slots, and frictional pivoting of the contacting members relative to the ends of the arms for adjustment. In one embodiment, each of the facing walls of the slot is provided with a raised bearing surface, and the side walls of the contacting member include indentations located to receive the raised bearing surfaces. In the other embodiment, the raised bearing surfaces are on the side walls of the contacting member and the corresponding indentations are provided on the facing walls of the slot.

Further according to the invention, a light source is provided for attachment to the forceps. Means are provided for supporting the light source for frictional pivotal and telescopic movement relative to the hinge, so that the light source can be positioned as needed with respect to the contacting members.

The invention may best be understood by reference to the following description and accompanying drawings which illustrate the invention. In the drawings.

Figure 1:
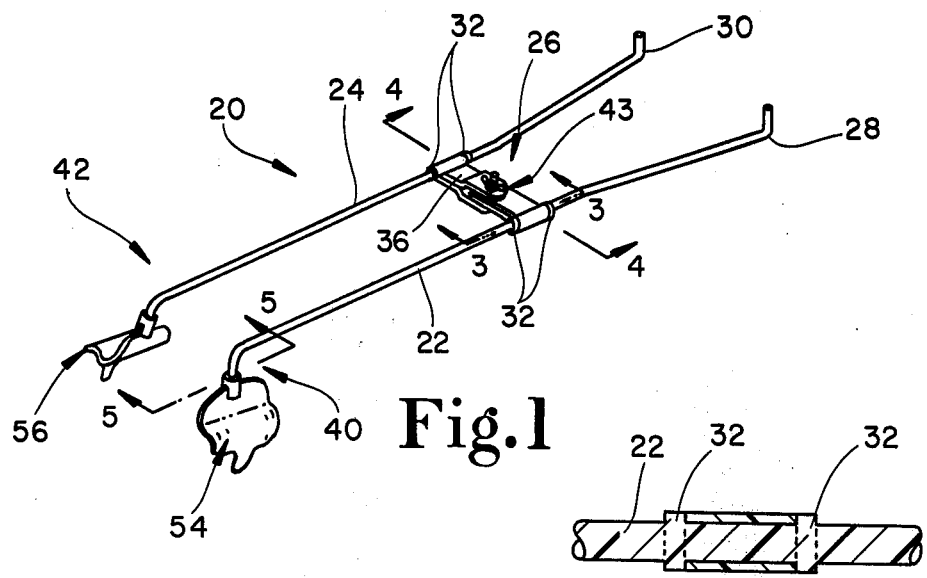
FIG. 1 is a perspective view of an apparatus constructed according to the present invention.

Referring particularly to FIG. 1, disposable plastic forceps 20 include a pair of elongated arms 22, 24 joined by a hinge 26. Each arm 22, 24 includes a proximal end portion 28, 30, respectively, providing a handle or hand grip for the forceps operator. Portions 28, 30 can be formed in any desired angle with respect to the remainder of arms 22, 24, to facilitate easy adjustment of the forceps.

Figure 3:
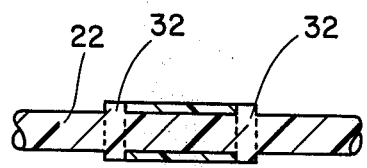
FIG. 3 is a fragmentary sectional view taken generally along section lines 3—3 of FIGS. 1-2.
Figure 4:
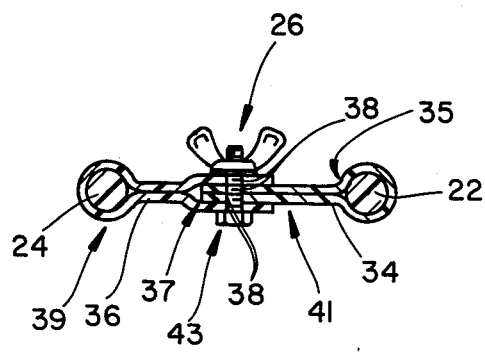
FIG. 4 is a fragmentary sectional view of the apparatus of FIGS. 1-2 taken along section lines 4—4 thereof.
Figure 2:
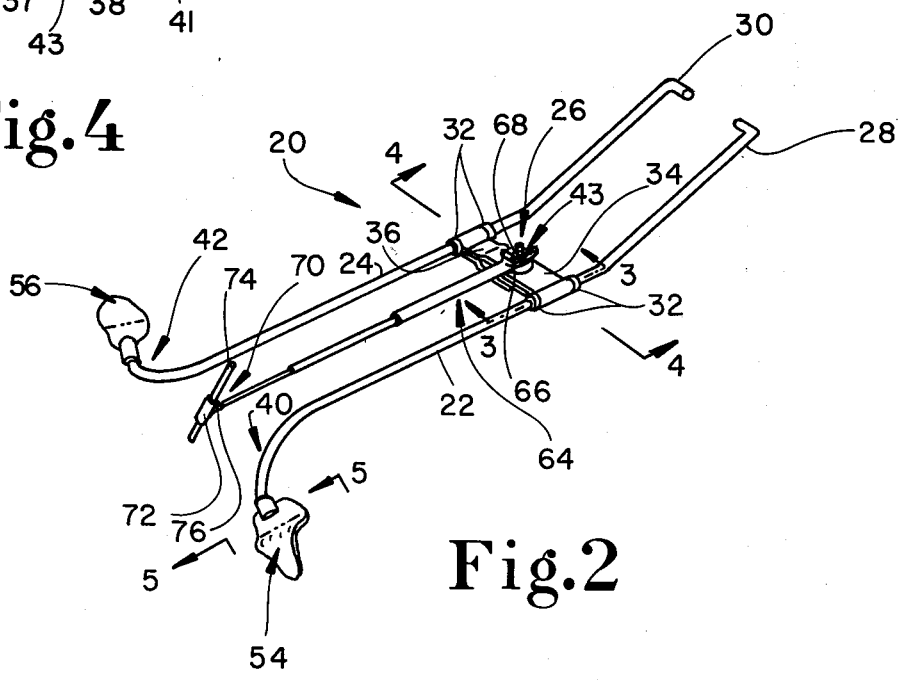
FIG. 2 is a perspective view of the apparatus of FIG. 1, in an adjusted configuration with an attachment provided in accordance with the present invention.
Figure 5:
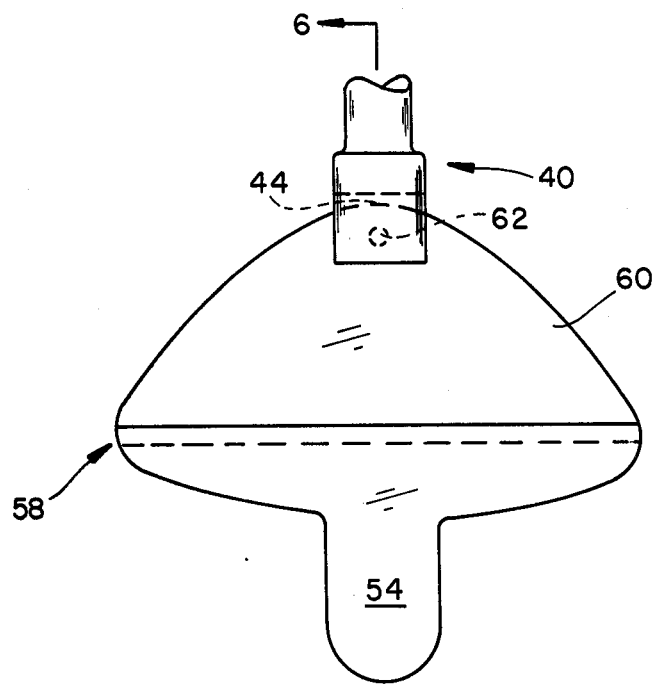
FIG. 5 is a fragmentary side elevational view of a detail of the apparatus of FIGS. 1-2.
Figure 6:
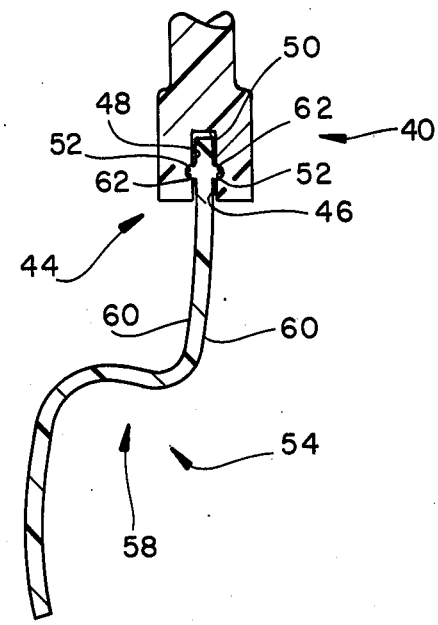
FIG. 6 is a fragmentary sectional view taken generally along section lines 6—6 of FIG. 5.
Figure 7:
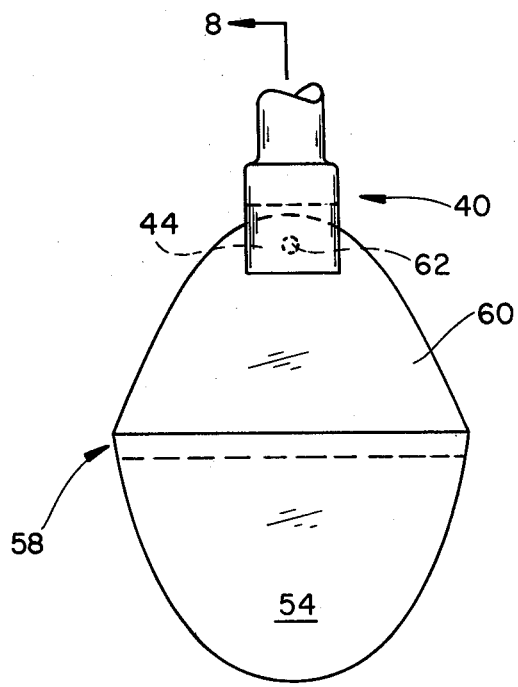
FIG. 7 is a fragmentary side elevational view of an alternative detail of the apparatus of FIGS. 1-2.
Figure 8:
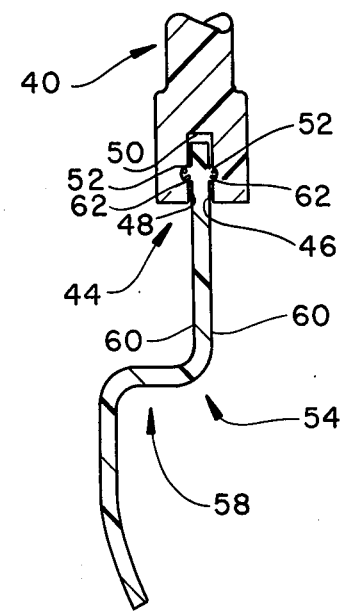
FIG. 8 is a fragmentary sectional view of the apparatus of FIG. 7 taken generally along section lines 8—8 thereof.
Figure 9:
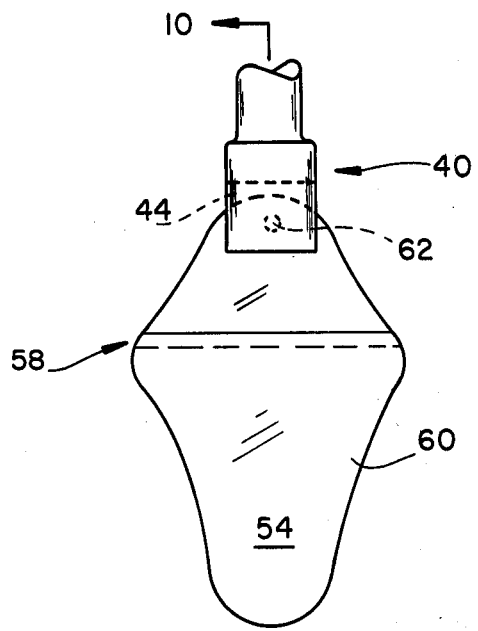
FIG. 9 is a fragmentary side elevational view of an alternative detail of the apparatus of FIGS. 1-2.
Figure 10:
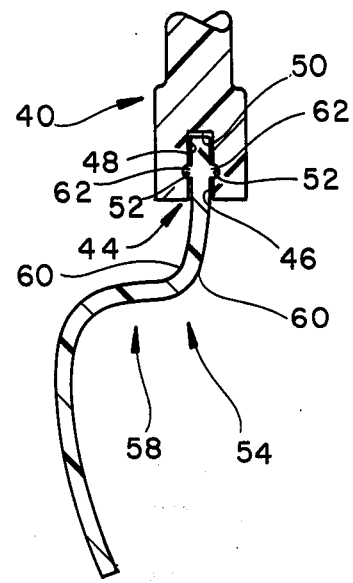
FIG. 10 is a fragmentary sectional view taken generally along section lines 10—10 of FIG. 9.
Figure 11:
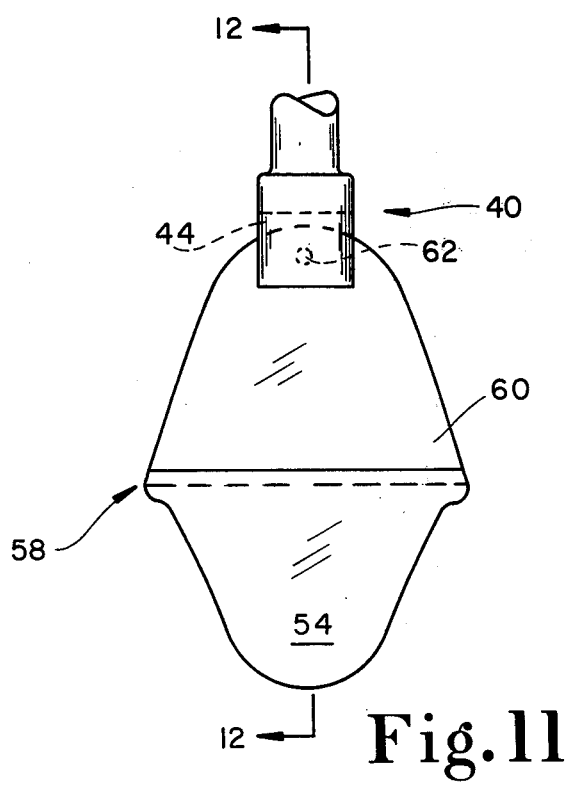
FIG. 11 is a fragmentary side elevational view of an alternative detail of the apparatus of FIGS. 1-2.
Figure 12:
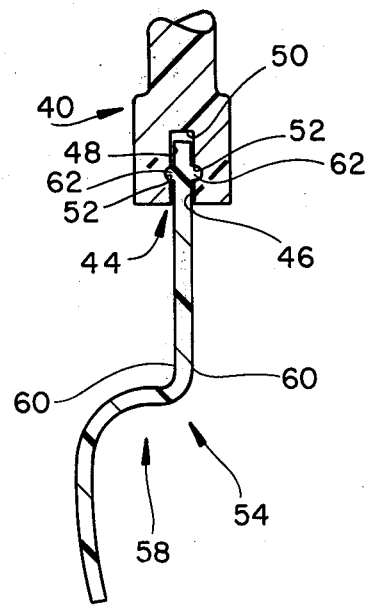
FIG. 12 is a fragmentary sectional view taken generally along section lines 12—12 of FIG. 11.
Figure 13:
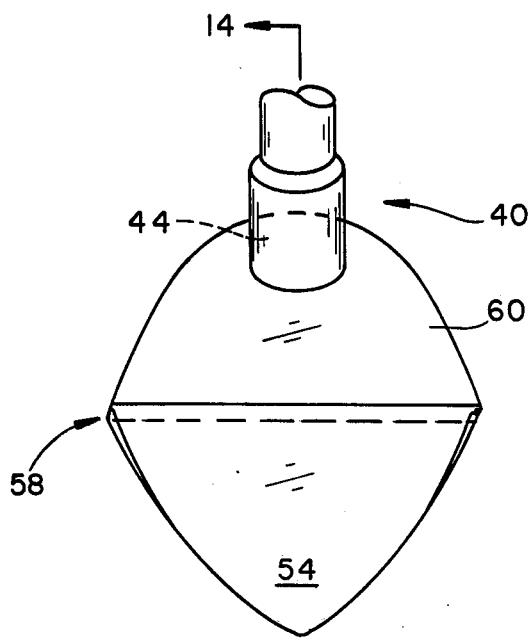
FIG. 13 is a fragmentary side elevational view of an alternative detail of the apparatus of FIGS. 1-2.
Figure 14:
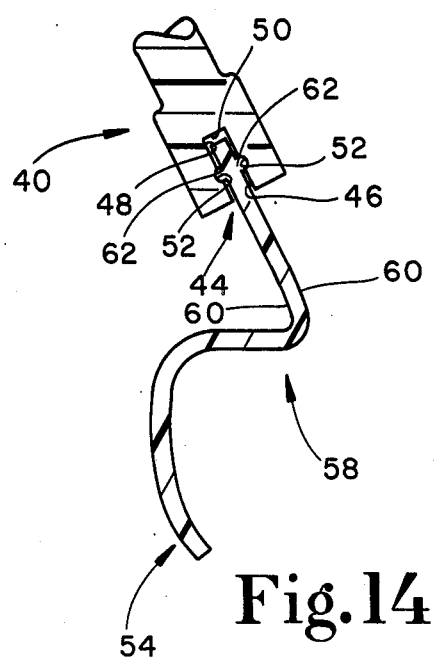
FIG. 14 is a fragmentary sectional view taken generally along section lines 14—14 of FIG. 13.
Figure 15:
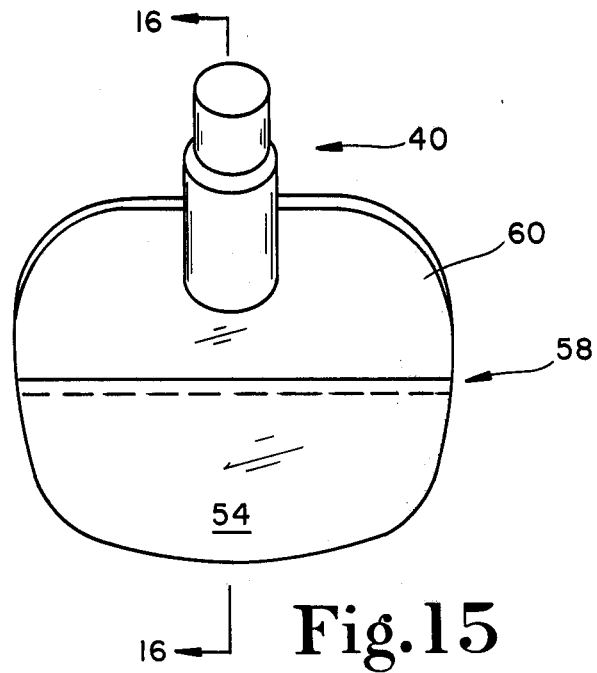
FIG. 15 is a fragmentary side elevational view of an alternative detail of the apparatus of FIGS. 1-2.
Figure 16:
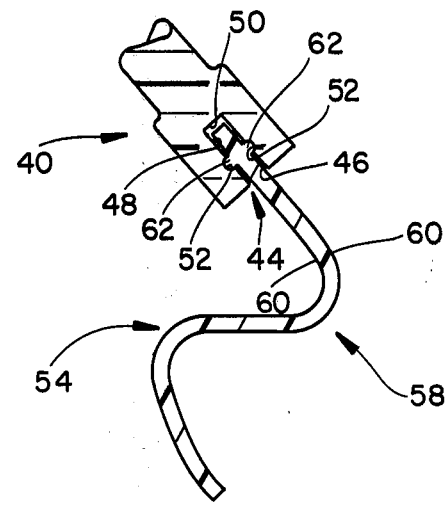
FIG. 16 is a fragmentary sectional view taken generally along section lines 16—16 of FIG. 15.
Figure 17:
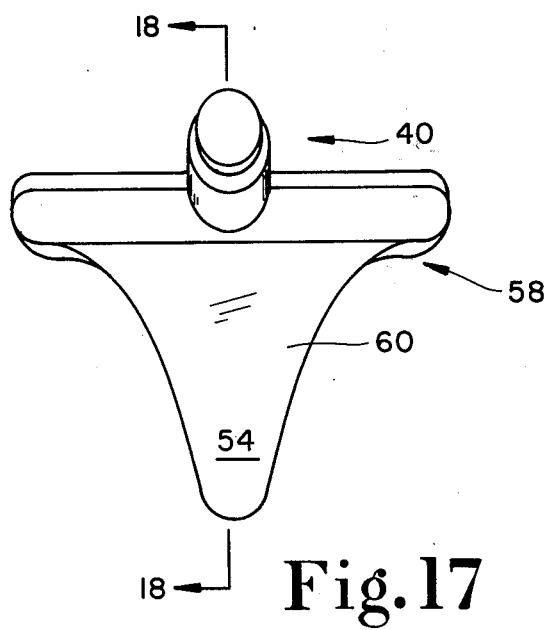
FIG. 17 is a fragmentary side elevational view of an alternative detail of the apparatus of FIGS. 1-2; and, FIG. 18 is a fragmentary sectional view taken generally along section lines 18—18 of FIG. 17.
Figure 18:
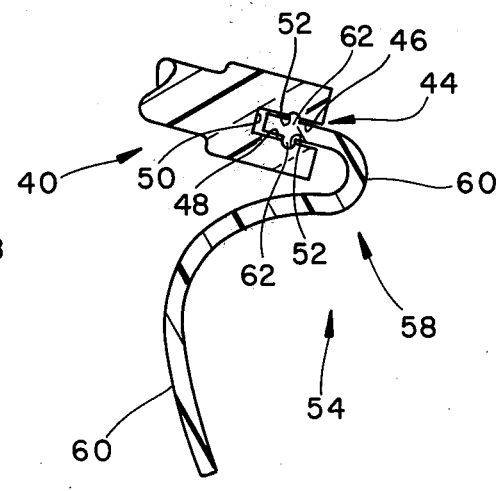

As best illustrated in FIG. 3, each of arms 22, 24 includes a pair of raised annular stops 32 on the intermediate portion of each of arms 22, 24. Stops 32 are spaced apart a predetermined distance to receive therebetween a plastic or metal strap 34 which is shaped as illustrated at 35 in FIG. 4 to conform to the contour of arm 22. Strap 34, when so shaped, rotatably and frictionally receives the intermediate portion of arm 22. The ends of strap 34 are flattened together as indicated at 37. A strap 36, which is also of metal or plastic, is received between stops 32 of arm 24, and is shaped as illustrated at 39 to the contour of the intermediate portion of arm 24. The ends of strap 36 are spaced apart as shown at 41 a sufficient distance so that the ends 37 of strap 34 will fit fairly tightly between them. The ends of both straps 34, 36 are provided with mating holes 38 to receive a bolt or hinge pin 43, thereby forming hinge 26. The bolt is secured in the hinge 26 by a wing nut 45 which is tightened to provide the desired frictional characteristics of hinge 26. It will be seen with reference to FIG. 2 that arms 22, 24 are thereby frictionally pivotally mounted from hinge 26 so that the arms can be turned to various configurations as needed by the forceps operator.

The distal end portions 40, 42 of arms 22, 24, respectively, are bifurcated to provide sockets or slots (see FIGS. 5-18) 44. Each slot 44 includes a pair of side walls 46, 48 and a bottom wall 50. In the illustrated embodiment, each of side walls 46, 48 is provided with a shallow recess or indentation 52. The forceps further include a pair of contacting members 54, 56, which are attached to arms 22, 24, respectively. Since the forceps 20 are useful in many different applications, it is desirable to have many different sizes and shapes of contacting members. Typically, however, to prevent forcing or slipping of the contacting members 54, 56 from the meatus or incision, the contacting members will have certain characteristics in common. For example, with reference to FIGS. 5-18, it will be seen that contacting members 54, 56 are all characterized by recurve- or double-bent portions 58. This recurve-bent configuration is useful in "hooking" the contacting members 54, 56 under the folds of tissue around the meatus or incision to "clamp" the forceps therein and prevent slippage of the forceps therefrom. It is understood that contacting members 56 of the pairs of contacting members, only one of which is illustrated in each of FIGS. 5-18 are "mirror-images" of the contacting members 54 illustrated in these Figs.

Each of contacting members 54, 56 in the illustrated embodiments is formed from a generally flat piece of plastic sheet stock. The recurve-bent portions 58 are formed in the flat stock by heating it sufficiently so that it becomes pliable, and bending it upon a forming jig. Before bending, of course, the stock is cut along a predetermined pattern to render the illustrated final shape of each of contacting members 54, 56 after bending. Each of contacting members 54, 56 includes a pair of oppositely facing side walls 60. A raised bearing surface 62 is formed on each of side walls 60. The orientations of surfaces 62 are such that they snap-fit into indentations 52 in side walls 46, 48 of slots 44. The flexibility of the material in arms 22, 24, respectively, and the tight snap-fit of contacting members 54, 56 into slots 44 insures a close frictional engagement of contacting members 54, 56 onto distal end portions 40, 42, respectively. Indentations 52 and raised bearing surfaces 62 are aligned so that contacting members 54, 56 can be pivoted about the axis of these aligned surfaces to provide the desired orientation of contacting members 54, 56 with respect to the distal ends of arms 22, 24, respectively. Of course, it must be understood that the raised bearing surfaces 62 can be provided on the side walls 46, 48 of slots 44 in the distal ends of arms 22, 24, and the indentations 52 can be provided on the side walls 60 of contacting members 54, 56 to achieve this same snap-fit frictional pivotal attachment of contacting members 54, 56 to arms 22, 24, respectively. Further, it should be understood that other attachment means, such as square cross-section sockets on the ends of arms 22, 24 and square cross-section projections molded onto contacting members 54, 56 can be used, although these do not provide the flexibility of attachment of contacting members 54, 56 to arms 22, 24 that the described arrangements provide.

Returning again to FIG. 2, a telescopic attachment 64 is provided. Attachment 64 includes a proximal end 66 shaped for attachment to hinge 26. The illustrated attachment 64 end 66 is attached to hinge 26 by passage of hinge pin 43 through the hole 68 in proximal end 66. However, other suitable attachment means, such as a clip, can be provided. Attachment 64 includes a distal end 70 with a sleeve 72 for receiving a lamp tube 74. Sleeve 72 is joined to the attachment 64 by a ball joint 76. The telescopic attachment 64 including ball joint 76 provides for orientation of the lamp tube 74 to illuminate any desired region of the meatus or incision which the forceps 20 is being used to dilate.

The disposable forceps of the instant invention are useful for holding open a body orifice or incision, and the contacting members 54, 56 are particularly suited to this function. Each contacting member includes the outwardly curved portion 58, as previously mentioned. These portions 58 are useful for hooking the contacting members under the tissue defining the orifice or incision to prevent slippage of the contacting members from the orifice or incision and the resulting closing of the orifice or incision. It is particularly advantageous to form the contacting members 54, 56 from a clear plastic material so that the walls of the orifice or incision may be seen through them. The contacting members 54, 56 also could be covered with a layer of some material which is capable of absorbing body fluids, such as blood. The absorbent material could be gauze or sponge or some similar material.

What is claimed is:

1. Disposable forceps including a pair of elongated arms, each having a proximal end portion providing a handle and a distal end portion including means for attachment of a contacting member removably to each of the arms, hinge means for movably joining the arms to one another about an axis other than one which is parallel to the longitudinal axes of said arms to provide adjustment of the forceps, and means for adjustably rotatably receiving the intermediate portion of each arm about the longitudinal axis of said arm and for holding the arms in adjusted position relative to the hinge means, the rotatable adjustment means being connected to the hinge means.

2. The invention of claim 1 wherein the distal end of each arm is formed to provide a slot for removably attaching one of the contacting members thereto.

3. The invention of claim 2 wherein the slot is defined by a pair of opposed walls, each wall including a raised bearing surface, and the contacting member includes side walls provided with corresponding indentations to provide a snap-fit of the contacting member into the slots, and to provide for frictional pivoting of the contacting members relative to the distal ends of the arms.

4. The invention of claim 2 wherein the slot is defined by a pair of opposed walls, each wall including an indentation, and the contacting members include side walls provided with corresponding opposed raised bearing surfaces to provide a snap-fit of the contacting members into the slots, and to provide for frictional pivoting of the contacting members relative to the ends of the arms.

5. The invention of claim 1 and further comprising a light source and means for supporting the light source for free pivotal and telescopic movement from the forceps.

6. Forceps including a pair of elongated arms, each having a proximal end portion providing a handle and a distal end portion including means for attachment of a contacting member to each of the arms, and a hinge means for movably joining the arms to one another about an axis other than one which is parallel to the longitudinal axes of said arms to provide adjustment of the forceps, the hinge means joining the arms intermediate their ends, means for adjustably rotatably attaching the hinge means to the intermediate portion of each arm about the longitudinal axis of said arm and means for holding the arms in adjusted position relative to the hinge means.

7. The invention of claim 6 wherein the distal end of each arm is formed to provide a slot for removably attaching one of the contacting members thereto.

8. The invention of claim 7 wherein the slot is defined by a pair of opposed walls, each wall including a raised bearing surface, and the contacting member includes side walls provided with corresponding indentations to provide a snap-fit of the contacting member into the slots, and to provide for frictional pivoting of the contacting members relative to the distal ends of the arms.

9. The invention of claim 7 wherein the slot is defined by a pair of opposed walls, each wall including an indentation, and the contacting members include side walls provided with corresponding opposed raised bearing surfaces to provide a snap-fit of the contacting members into the slots, and to provide for frictional pivoting of the contacting members relative to the ends of the arms.

10. Disposable forceps for holding open a body orifice or incision, the forceps including a pair of contacting members and a pair of elongated arms, each arm having a proximal end portion providing a handle and a distal end portion formed for removable attachment of a respective contacting member thereto, and a hinge means for movably joining the arms to one another intermediate their ends and about an axis other than one which is parallel to the longitudinal axes said arms, means for adjustably rotatably receiving the intermediate portion of each arm about the longitudinal axis of said arm and for holding the arms in adjusted position relative to the hinge means, the rotatable adjustment means being connected to the hinge means, each contacting member including an outwardly-bent portion for hooking the contacting members under the tissue defining the orifice or incision to prevent slippage of the contacting members from the orifice or incision and resulting closing of the orifice or incision, the distal end portion providing a pair of opposed walls defining a slot, the contacting members being sized for insertion into respective slots, one of the pair of opposed walls and contacting members providing a pair of aligned, raised bearing surfaces, and the other of the pair of opposed walls and contacting members providing a pair of aligned indentations for engagement by the bearing surfaces to provide a snap-fit and frictional pivoting of the contacting members relative to the ends of their respective arms.

* * * * *